(12) United States Patent
Brogaard et al.

(10) Patent No.: US 10,113,989 B2
(45) Date of Patent: Oct. 30, 2018

(54) SULPHITE SENSOR AND METHOD FOR MEASURING SULPHITE CONCENTRATION IN A SUBSTANCE

(71) Applicant: General Electric Company GmbH, Baden (CH)

(72) Inventors: Fredrik Jens Brogaard, Växjö (SE); Mikael Larsson, Mölndal (SE); Fredrik Winquist, Linköping (SE)

(73) Assignee: General Electric Technology GmbH, Baden (CH)

( * ) Notice: Subject to any disclaimer, the term of this patent is extended or adjusted under 35 U.S.C. 154(b) by 279 days.

(21) Appl. No.: 14/347,393

(22) PCT Filed: Oct. 8, 2012

(86) PCT No.: PCT/IB2012/055433
§ 371 (c)(1),
(2) Date: Mar. 26, 2014

(87) PCT Pub. No.: WO2013/050990
PCT Pub. Date: Apr. 11, 2013

(65) Prior Publication Data
US 2014/0231272 A1  Aug. 21, 2014

(30) Foreign Application Priority Data
Oct. 7, 2011  (EP) .................................... 11184432

(51) Int. Cl.
*G01N 27/48*    (2006.01)
*G01N 27/416*   (2006.01)
(Continued)

(52) U.S. Cl.
CPC ......... *G01N 27/4162* (2013.01); *G01N 21/93* (2013.01); *G01N 33/0029* (2013.01)

(58) Field of Classification Search
None
See application file for complete search history.

(56) References Cited

U.S. PATENT DOCUMENTS

| | | | |
|---|---|---|---|
| 4,336,035 A | 6/1982 | Evenstad et al. | |
| 4,336,102 A | 6/1982 | Jacobs et al. | |

(Continued)

FOREIGN PATENT DOCUMENTS

| | | |
|---|---|---|
| CN | 85204611 U | 7/1986 |
| CN | 201320718 Y | 10/2009 |

(Continued)

OTHER PUBLICATIONS

Wold, S., Esbensen, K. and Geladi, P. "Principal component analysis: A tutorial." Chemometrics and Intelligent Laboratory Systems 2, 37-52, 1987.*

(Continued)

*Primary Examiner* — Gurpreet Kaur
*Assistant Examiner* — Steven E Rosenwald
(74) *Attorney, Agent, or Firm* — Armstrong Teasdale LLP; Adam R. Wuller; Rita D. Vacca (57) ABSTRACT

The present invention relates to a method for measuring a concentration of sulphite in a substance in a gas cleaning process, the method comprising the steps of sending a plurality of voltage pulses through the substance by a first electrode (11) and a second electrode (20), which first and second electrodes (11, 20) are in contact with the substance, receiving current responses generated by the plurality of voltage pulses, and analyzing the current responses using a multivariate data analysis for calculation of the concentration of sulphite in the substance. The present invention further relates to a sulphite sensor (1) for performing such a method.

8 Claims, 8 Drawing Sheets

(51) Int. Cl.
*G01N 21/93* (2006.01)
*G01N 33/00* (2006.01)

(56) References Cited

U.S. PATENT DOCUMENTS

| | | | |
|---|---|---|---|
| 4,502,872 | A | 3/1985 | Ivester et al. |
| 1,659,832 | A | 6/1991 | Nelson |
| 5,569,436 | A | 10/1996 | Lerner |
| 6,403,256 | B1 | 6/2002 | Gan et al. |
| 7,625,537 | B2 | 12/2009 | Rader et al. |
| 2011/0206813 | A1 | 8/2011 | Shen et al. |
| 2017/0023507 | A1 | 1/2017 | Håkansson |

FOREIGN PATENT DOCUMENTS

| | | | | |
|---|---|---|---|---|
| CN | 102128862 A | | 7/2011 | |
| EP | 0162536 A1 | | 11/1985 | |
| EP | 1219957 A1 | | 7/2002 | |
| EP | 1 010 005 B1 | | 7/2008 | |
| EP | 2 110 660 A1 | * | 10/2009 | ............ G01N 27/38 |
| JP | 0275322 A | | 3/1990 | |
| JP | 05317643 A | | 12/1993 | |
| JP | 06182148 A | | 7/1994 | |
| JP | 11104448 A | | 4/1999 | |
| JP | 2948330 B2 | | 9/1999 | |
| SU | 1659832 A1 | | 6/1991 | |
| TW | 524717 | | 3/2003 | |
| WO | WO 99/13325 | * | 3/1999 | ........... G01N 27/416 |
| WO | 0244460 A1 | | 6/2002 | |
| WO | 02052254 A1 | | 7/2002 | |
| WO | 03046554 A1 | | 6/2003 | |
| WO | 2004/053476 A1 | | 6/2004 | |

OTHER PUBLICATIONS

S. Wold, M. Sjostrom and L. Eriksson "PLS-regression: a basic tool of chemometrics" Chemometrics and Intelligent Laboratory Systems, 58 (2001) 109-130.*

Adeloju et al. (Electroanalysis, 6, 1994, 865-870).*

Heering et al. (Anal. Chem. 1999, 71, 174-182).*

Bott (Current Separations, 16:1, 1997).*

"Kinetics and mechanism of sulphite oxidation on a rotating platinum disc electronic in an alkaline solution"— E. Skavas etal, Electrochimica Acta vol. 52, pp. 3510-3517 dated Nov. 22, 2006.

"The electrochemical reaction of Sulphur-oxygen compounds—Part II. Voltammetric investigation performed on platinum"— T. Hemmingsen, Electrochimica Acta vol. 37 No. 15, pp. 2785-2790 dated Dec. 31, 1992.

Woodis et al—"Volumetric method for control of ammonia scrubbing process for removal of sulfur dioxide form stack gases"— Environmental Science & Technology , vol. 7, No. 9, Sep. 1, 1973.

Garber et al—"Determination of atmospheric sulfur dioxide by differential pulse polarography"—Analytical Chemistry, vol. 44, No. 8, Jul. 1, 1972.

Labrador et al—"Determination of Bisulfites in Wines with an Electronic Tongue Based on Pulse Voltammetry"—Electroanalysis 2009, 21, No, 3-5, 612-617.

Winquist et al—"An electronic tongue based on voltammetry"— Analytica Chimica Acta 357 (1997) 21-31.

European Search Report corresponding to EP Appln. No. 11184432.0, dated Mar. 7, 2012.

The International Search Report and the Written Opinion of the International Searching Authority corresponding to PCT Appln. No. PCT/IB2012/055433 dated Jan. 16, 2013.

Winquist et al., "Electronic Tongues", MRS Bulletin, pp. 1-6, vol. No. 29, Issue No. 10, Oct. 2004.

Unofficial English Translation of Chinese Office Action issued in connection with corresponding CN Application No. 201280053533.5 dated Mar. 31, 2015.

Lee Y J et al, "Oxidative degradation of organic acid conjugated with sulfite oxidation in flue gas desulfurization: Products, kinetics, and mechanism", Environmental Science & Technology, 1987, pp. 266-272, vol. 21—No. 3.

* cited by examiner

SULPHITE SENSOR AND METHOD FOR MEASURING SULPHITE CONCENTRATION IN A SUBSTANCE

This is a US National Phase application claiming priority to International Application No. PCT/IB2012/055433 having an International Filing Date of Oct. 8, 2012, and EP Application No. 11184432.0 having a Filing Date of Oct. 7, 2011, each incorporated herein in its entirety by reference.

TECHNICAL FIELD

The present invention relates to a method for measuring a concentration of sulphite in a substance in a gas cleaning process.

The present invention further relates to a sulphite sensor adapted for measuring the concentration of sulphite in a substance in a gas cleaning device.

BACKGROUND

Process gases containing acid gases are generated in many industrial processes. Such an industrial process may be the combustion of a fuel such as coal, oil, peat, waste, etc., in a combustion plant such as a power plant, whereby a hot process gas or "flue gas" is generated containing pollutants including acid gases. The process gas needs to be treated for removal of at least a portion of the acid gases. Such treatment may be provided in a wet scrubber such as disclosed in EP 0 162 536. The disclosed wet scrubber comprises an absorption liquid, which is brought into contact with the process gas to absorb at least a portion of the acid gases. For example, the absorption liquid may be atomized through nozzles to react with the process gas.

The treatment process may be controlled based on a feedback of information concerning the status of the treatment process. Such information may include measured properties of the absorption liquid. A common manner of controlling a wet scrubber is to measure the pH level in the absorption liquid and thereby provide information that may be used for controlling the supply of fresh absorbent, such as limestone, to the absorption liquid.

However, measurements of the pH level in an absorption liquid are not reliable. The pH measurement is a difficult procedure that may provide unreliable information on the properties of the absorption liquid. This reduces the accuracy of the control of the treatment process and the efficiency of the wet scrubber.

Consequently, there is a need for a more reliable measurement of the properties of an absorption liquid in a gas cleaning device for controlling the treatment process of cleaning a process gas.

SUMMARY

An object of the present invention is to provide an improved method relative to prior art, by which reliable information on the properties of a substance in a gas cleaning process is provided.

This object is achieved by means of a method for measuring a concentration of sulphite in a substance in a gas cleaning process, the method comprising the steps of sending a plurality of voltage pulses through the substance by a first electrode and a second electrode, which first and second electrodes are in contact with the substance, receiving current responses generated by the plurality of voltage pulses, and analyzing the current responses using multivariate data analysis for calculation of the concentration of sulphite in the substance.

An advantage of this method is that the sulphite level in the substance may be measured in a reliable way. Further, by the present method a low concentration of sulphite may be measured with high accuracy. Thereby, the gas cleaning process may be controlled with high accuracy. If the substance is an absorption liquid in a wet scrubber, for example a wet scrubber using limestone as absorbent, the method according to the invention may provide a reliable measurement of sulphite concentration in the absorption liquid, providing an input for controlling the treatment process of a process gas in the wet scrubber. The method may use a voltammetric method. In the present method, voltage pulses may be sent over a first and a second electrode in the substance. The second electrode may be a large piece of metal. The second electrode may have an area, which is at least 20 times larger than that of the first electrode. The current responses generated by the voltage pulses are treated by using multivariate data analysis, mathematical models from samples with known sulphite concentrations may be used for creating a prediction model that may be used for determining the sulphite concentration in an unknown substance.

According to one embodiment the step of sending a plurality of voltage pulses may comprise sending the plurality of voltage pulses in a series, stepwise increasing and/or decreasing the voltage level.

By increasing and/or decreasing the voltage level stepwise, a series of voltages sent through the first electrode may get the shape of a staircase. A voltage pulse generating a current response may occur when the voltage level is increased or decreased to a new level. During a measurement of a sulphite concentration, the voltage levels may be swept in steps from a first voltage level to a final voltage level. The first voltage level may be a negative voltage and the final voltage level a positive voltage, resulting in an anodic sweep. Alternatively, the first voltage level may be positive and the final voltage level may be negative, resulting in a cathodic sweep.

According to one embodiment the step of analyzing the current responses comprises analyzing peaks of the current responses using multivariate data analysis.

An advantage of this embodiment is that multivariate data analysis is an efficient manner of obtaining a measurement of the sulphite concentration from information available in the current responses.

According to one embodiment, the step of analyzing the current responses may comprise analyzing a peak value and at least one more value of each current responses using multivariate data analysis.

When measuring sulphite in a substance, a series of voltages are sent through the first electrode, resulting in a series of current responses. The peak shape of each current response may provide information regarding the sulphite in the substance. The current response may include a peak level and a decay of the current. Each current response may be sampled in a number of samples providing a number of values. Analyzing the peak value and at least one more value of each current response may be enough for using the multivariate data analysis to estimation of the sulphite concentration in the substance. The amount of data handled in the analysis is thereby reduced compared to analyzing a complete peak or a large number of data values, i.e. all sample values. Using only the two values may still provide a reliable measurement of the sulphite concentration. Sulphite may have a redox potential at which a current response may be increased compared to other potentials. When a series of voltage pulses approach a voltage level corresponding to the redox potential of sulphite, the current response may provide a peak shaped increased current level. Such increased current level may be identified when analyzing the peak value of each current response. In one embodiment, the at least one value besides the peak value may be four values. Such values may be taken at the decay of the current response to provide further information regarding the sulphite level in the substance. As an example, each current response may be sampled in 50 samples. If five values, including the peak value, may be analyzed using multivariate data analysis, three of the values, including the peak value, may be taken from the first third of the samples. Further, one value may be taken from a second third of the samples, and one value may be taken from a last third of the samples. In one embodiment, the peak value may be from the first or second sample of each current response.

According to one embodiment the method may further comprise cleaning a surface of the first electrode from a coating caused by the contact between the first electrode and the substance.

The first electrode may be made of platinum. When measuring a substance containing sulphurous compounds, the first electrode may rather quickly become unusable due to sulphides binding to a platinum surface of the electrode. This may form a coating on the electrode surface and negatively affect the result of the measurement. By cleaning the surface of the electrode, the coating may be removed to ensure the reliability of the measurement. The cleaning of the electrode may be made continuously, or semi-continuously. The cleaning may be performed by a cleaning unit, such as a brush, a grinder, a scraper or the like.

According to one embodiment the amount of each voltage pulse sent through the substance may be 0.02-0.2 V higher or lower than an immediately preceding voltage pulse.

Each voltage pulse may be an increase or decrease of the voltage level. The voltage level may be increased or decreased with an amount of between 0.02-0.2 V for each voltage pulse. Preferably, the voltage level may be increased or decreased with an amount of about 0.05 V. A complete measurement of sulphite in the substance may for instance start with a voltage of −0.9 V, which is in a stepwise manner increased up to 0.8 V. A current response may be received for each voltage pulse or step. After a voltage sweep, a plurality of current responses may have been received. Each current response is peak shaped and the first and the last current values may be analyzed using multivariate data analysis. By providing a stepwise voltage sweep, the plurality of current responses may provide reliable information regarding the concentration of sulphite in the substance.

According to one embodiment the step of cleaning a surface of the first electrode may comprise rotating a cleaning unit in contact with the first electrode.

A cleaning unit may be rotated in contact with the first electrode, providing a continuous cleaning of the electrode. Coatings formed on the surface of the electrode may thereby continuously be removed. The cleaning of the electrode may be brushing, grinding, scraping or the like of the electrode. The first electrode may be ring shaped for providing an extended contact with the substance. A ring shaped first electrode may further provide continuous contact with the rotating cleaning unit.

According to one embodiment the cleaning unit may be rotated in contact with a surface of the first electrode at a speed of 2-40 rpm.

By rotating the cleaning unit in contact with a surface of the first electrode at a speed of about 2-40 rpm, the coatings on the surface of the first electrode may be removed continuously, and measurement may be performed in a reliable way. The cleaning unit may not interfere with the sending of voltage pulses. Preferably, the cleaning unit may be rotated at a speed of about 15 rpm. The rotating speed of the cleaning unit may vary over time, providing speed intervals for the cleaning unit.

According to one embodiment the substance may be an absorption liquid utilized in a wet scrubber cleaning process.

In a gas cleaning process such as in a wet scrubber adapted to clean process gases, an absorption liquid, for example a limestone based absorption liquid, may be provided to react with acid gases in the process gas. Such acid gases may comprise sulphur dioxide. The reaction may result in that the absorption liquid contains sulphite. The concentration of sulphite in the absorption liquid may provide information of the status of the gas cleaning process, which information may be used for controlling the wet scrubber. By providing a reliable sulphite measuring method for the absorption liquid, the wet scrubber may be controlled in a reliable way.

According to a further aspect, there is provided a sulphite sensor for measuring the concentration of sulphite in a substance in a gas cleaning device, wherein the sulphite sensor comprises a first electrode and a second electrode adapted to be in contact with the substance, a control unit adapted to send voltage pulses through the substance by the first electrode and the second electrode, and an analyzing unit adapted to receive and analyze current responses generated by the voltage pulses, wherein said analyzing unit is adapted to perform multivariate data analysis.

An advantage with this sulphite sensor is that a reliable measurement of sulphite concentration in a substance may be performed. The measurement may then be used for controlling the gas cleaning process. The sulphite concentration may be measured reliably even when the sulphite concentration is very low. Voltage pulses may be sent by the control unit through the first electrode into the substance. The current responses generated by the voltage pulses may be received through a second electrode. The second electrode may be a piece of metal. By using multivariate data analysis in the analyzing unit, mathematical models from samples with known sulphite concentrations may be used for creating a prediction model that may be used for determining the sulphite concentration in an unknown substance.

According to one embodiment the control unit may be adapted to send the voltage pulses in a series, such that a voltage level may be increased and/or decreased in a stepwise manner with each voltage pulse.

By increasing and/or decreasing the voltage level stepwise, a series of voltage pulses sent through the first electrode may get the shape of a staircase. The voltage pulses generating the current responses may occur when the control unit increases or decreases the voltage level to a new level. The sulphite sensor may be adapted to sweep the voltage level in steps from a first voltage level to a final voltage level for measurement of the sulphite level. The first voltage level may be a negative voltage and the final voltage level may be a positive voltage, resulting in an anodic sweep. Alternatively, the first voltage level may be positive and the final voltage level may be negative, resulting in a cathodic sweep.

According to one embodiment the analyzing unit may be adapted to perform a multivariate data analysis based on peaks of the current responses.

Figure 4A:
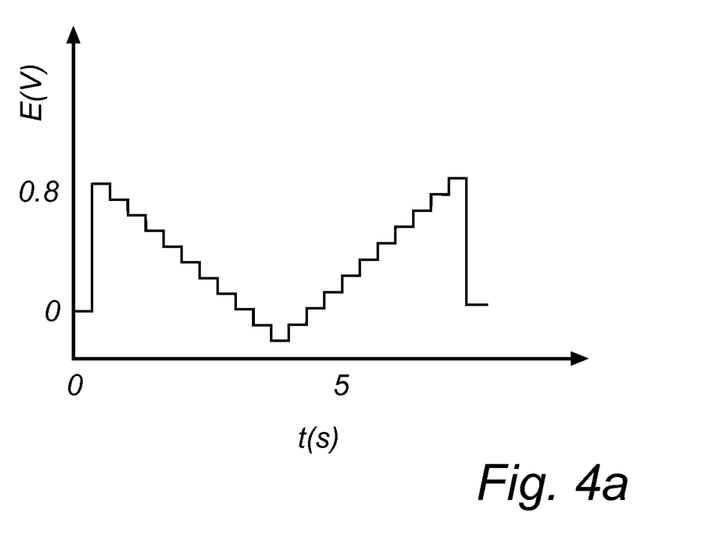
FIG. 4a is a graph of voltage level over time from a method according to an embodiment.

A peak of the current response may provide information regarding the sulphite in the substance. The current response may include a peak level and a decay of the current towards zero. If the analyzing unit analyzes the peak of the current response, a reliable measurement of the sulphite concentration may be achieved. Sulphite may have a redox potential at which a current response may be increased compared to other potentials. If voltage pulses sent by the control unit correspond to the redox potential of sulphite, the current response peak may provide an increased current level. When measuring in crude and complex media, as liquid from a gas cleaning process, however, no clear peaked current levels at the redox potential may be obtained. This is due to interfering, more or less redox active substances in the measuring media resulting in a very complex current response. This makes the current response from a measurement very difficult to interpret. Thus, to interpret data from a current spectrum, multivariate data analysis are used. Training sets of current spectra with known sulphite concentrations are then used to make mathematical prediction functions for samples with unknown concentration of sulphite. An example of a current spectrum is shown in FIG. 4c.

According to one embodiment the sulphite sensor may further comprise a cleaning unit adapted to clean the first electrode.

The first electrode may be made of platinum. When using the sulphite sensor for measuring a substance containing sulphurous compounds, the first electrode may rather quickly become unusable due to sulphides binding to a platinum surface of the electrode. This may form a coating on the first electrode surface and negatively affect the result of the measurement. By providing the sulphite sensor with a cleaning unit, the coating on the surface of the electrode may be removed, to ensure the reliability of the sensor. The cleaning unit may be adapted to clean the first electrode in a continuous or semi-continuous manner during the measurement of sulphite. The cleaning unit may be a brush, a grinder, a scraper or the like.

BRIEF DESCRIPTION OF THE DRAWINGS

The invention is described in more detail with reference to the drawings, in which.

DETAILED DESCRIPTION OF EMBODIMENTS

The present invention is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

Figure 1:
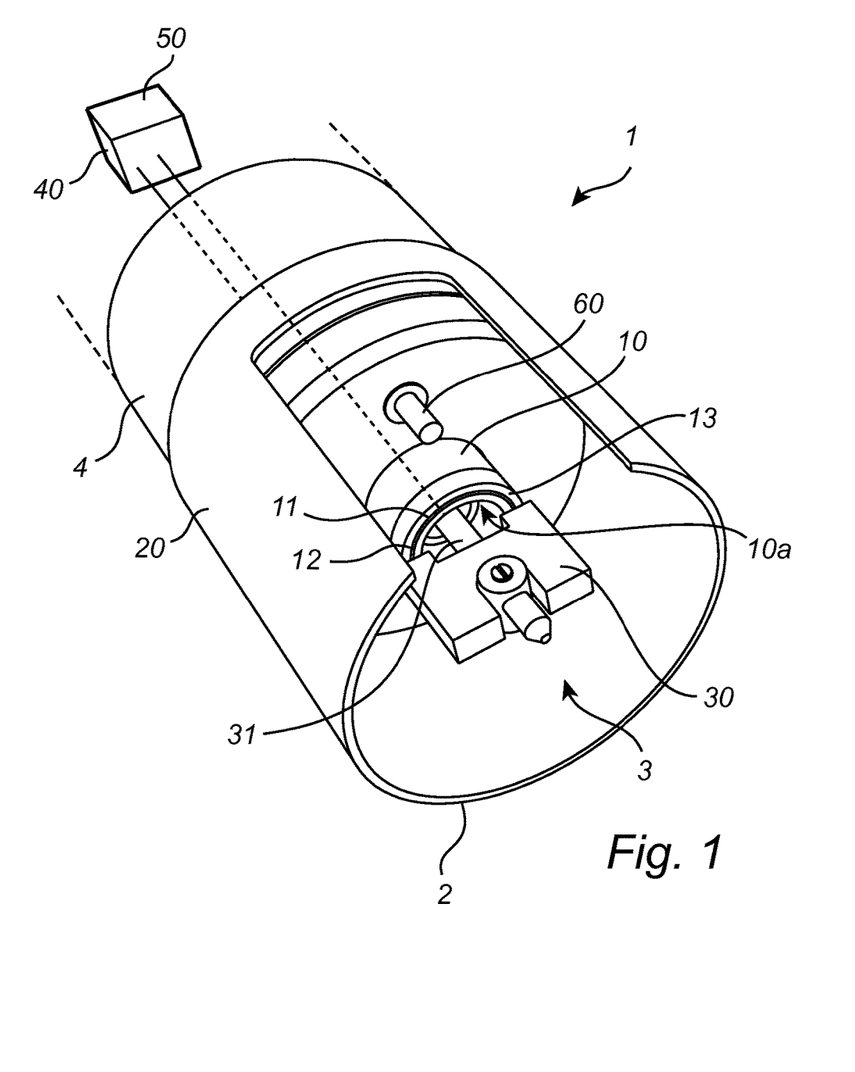
FIG. 1 is a perspective view of a sulphite sensor according to an embodiment.
Figure 2:
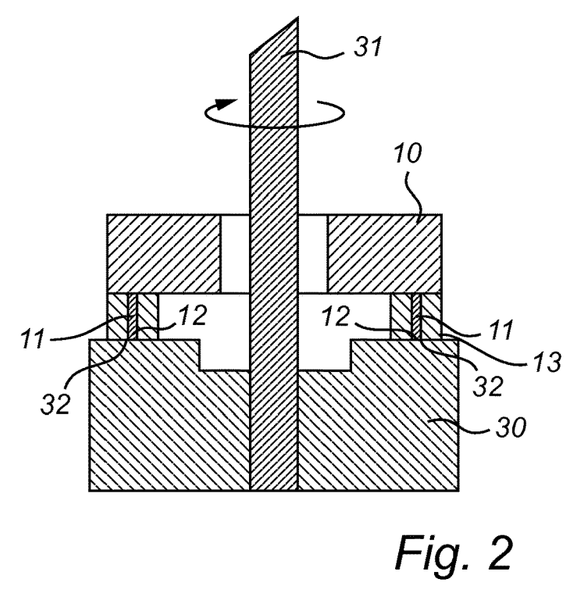
FIG. 2 is a schematic cross-sectional side view of a sulphite sensor.

A sulphite sensor 1 according to the invention is illustrated in a perspective view in FIG. 1 and in a schematic cross-sectional side view in FIG. 2. The sulphite sensor 1 comprises a base section 4, and a cover 2 that forms sides of a space 3 for sulphite detection. A sensor head 10 is located in the space 3. The sensor head 10 is formed as a tube extending into the space 3. At an axial end portion 13 of the sensor head 10, a first electrode 11 having the form of a platinum ring is provided. A surface 12 of the first electrode 11 is level with the axial end portion 13 of the sensor head 10.

A shaft 31 extends through interior 10a of the tube shaped sensor head 10. The shaft 31 is rotated by an electric motor (not shown). The shaft 31 is coupled to a grinding unit 30. The grinding unit 30 has a surface 32, which is best shown in FIG. 2, adapted to abut the surface 12 of the first electrode 11. The shaft 31 rotates the grinding unit 30 such that the surface 32 of the grinding unit 30 grinds/cleans the surface 12 of the first electrode 11. The grinding unit 30 rotates in contact with the surface 12 of the first electrode 11 at a speed of 2-40 rpm, preferably at a speed of 15 rpm. The grinding unit 30 is preferably made of a ceramic material based on e.g. silicon carbide or silicon nitride.

The sulphite sensor 1 further comprises a second electrode 20. The second electrode 20 is preferably of a metal, such as steel or the like. The second electrode 20 is located at a distance from the first electrode 11. In the illustrated embodiment, the second electrode 20 is constituted by the metal cover 2.

A control unit 40 is arranged in the sulphite sensor 1 or connected to the sulphite sensor 1 and is adapted to send voltage pulses through the substance occupying the space between the first electrode 11 and the second electrode 20. When the sulphite sensor 1 is submerged into a substance, the voltage pulses enter the substance via the first electrode 11. The second electrode 20 is adapted to receive current responses generated by said voltage pulses and pass the current responses back to the control unit 40. The control unit 40 receives and analyzes using an analyzing unit 50 the current responses and calculates a concentration of sulphite in the substance using a multivariate data analysis. By using multivariate data analysis in the analyzing unit 50, mathematical models from samples with known sulphite concentrations is used for creating a prediction model that is used for determining the sulphite concentration in an unknown substance.

Data from voltammetric measurements are often difficult to interpret. Each measurement consists of a number of variables. Multivariate data analyzing methods, such as principal component analysis (PCA) and projection to latent structure (PLS), as is known from, for example: Wold, S., Esbensen, K. and Geladi, P. "Principal component analysis: A tutorial." Chemometrics and Intelligent Laboratory Systems 2, 37-52, 1987; and from: S. Wold, M. Sjöström and L. Eriksson "PLS-regression: a basic tool of chemometrics" Chemometrics and Intelligent Laboratory Systems, 58 (2001) 109-130, have shown to be useful. PCA is a mathematical tool, which describes the variance in experimental data. A vector is calculated which describes the direction of the largest variance in experimental data, that is the direction that describes the largest differences between observations. This vector is called the first principal component. The second principal component is orthogonal to and thus independent of the first principal component. Further principal components can be calculated in a similar way, until most of the observations are explained. A new matrix, as defined by the principal components is then formed, and the data set is considerably reduced, depending on the significance of the different principal components, but in many cases only to two dimensions. The loading vectors describe the direction of the principal components in relation to the original variables, and the score vectors, describe the direction of the principal components in relation to the observations. Thus, a score plot can be made, showing the relationships between the original samples and how much they influence the system. Thus, a score plot shows the relationships between the experiments, and groupings of them can be used for classification.

PLS is used to make models from calibration sets of data. It is a linear method, in which PCA is performed on both the X-data (the voltammogram) and the Y-data (the concentrations). Then a linear regression is performed on each PC between the datasets and the Y-data, giving a regression model. This model can be used to predict values from the voltammograms.

Further information regarding multivariate data analysis may be found in I. T. Jolliffe "Principle Component Analysis" Springer-Verlag, New York inc. (1986) ISBN 0-387-96269-7, or K. R. Beebe, R. J. Pell and M. B. Seasholtz "Chemometrics—A practical guide" John Wiley & Sons Inc. (1998) ISBN 0-471-12451-6.

In one embodiment, the sulphite sensor 1 further comprises a temperature sensor 60 for measuring the temperature of the substance.

Figure 3:
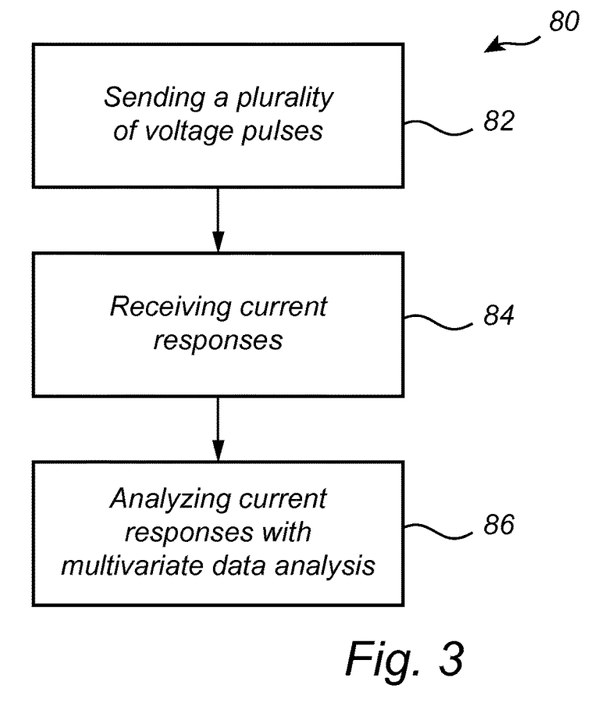
FIG. 3 is a flow chart of a method of measuring sulphite in a substance.

FIG. 3 is a flow chart of a method 80 for measuring a concentration of sulphite in a substance. The substance may be provided in a gas cleaning process. In a step 82, a plurality of voltage pulses is sent through the first electrode 11. The first electrode 11 is in contact with the substance. Voltage pulses are sent from the control unit 40 by the first electrode 11 and the second electrode 20 through the substance as a stepwise increasing or decreasing voltage level as shown in FIG. 4a. A staircase pattern of the voltage level sent through the first electrode 11 is formed. Each step involves increasing or decreasing the voltage level by, preferably, about 0.05 V. In an example of the method, the voltage level sent through the substance as voltage pulses is, in a stepwise manner, increased from a voltage level of −1.0 V to a voltage level of 1.0 V in steps of 0.05 V. In a further example, illustrated in FIG. 4a, the voltage level is first decreased from 0.8 V and down to −0.1 V, in steps of 0.05 V, and is then increased from −0.1 V and up to 0.8 V, in steps of 0.05 V.

In a step 84, current responses are received, which current responses are generated by the voltage pulses sent by the first electrode 11 to the second electrode 20. The current responses are received by the second electrode 20. The second electrode 20 is also in contact with the substance. Each step of increasing or decreasing the voltage level generates a new current response in the second electrode 20.

In a final step 86, the current responses are analyzed using a multivariate data analysis. The concentration of sulphite in the substance may thereby be measured based on the current responses. According to one embodiment, all of the plurality of current responses is used for the measurement of sulphite concentration in the substance. In one embodiment, the current response is analyzed after each sent voltage pulse. Alternatively, a series of voltage pulses are sent, generating a series of current responses, before multivariate data analysis is performed on the series of current responses.

Figure 4B:
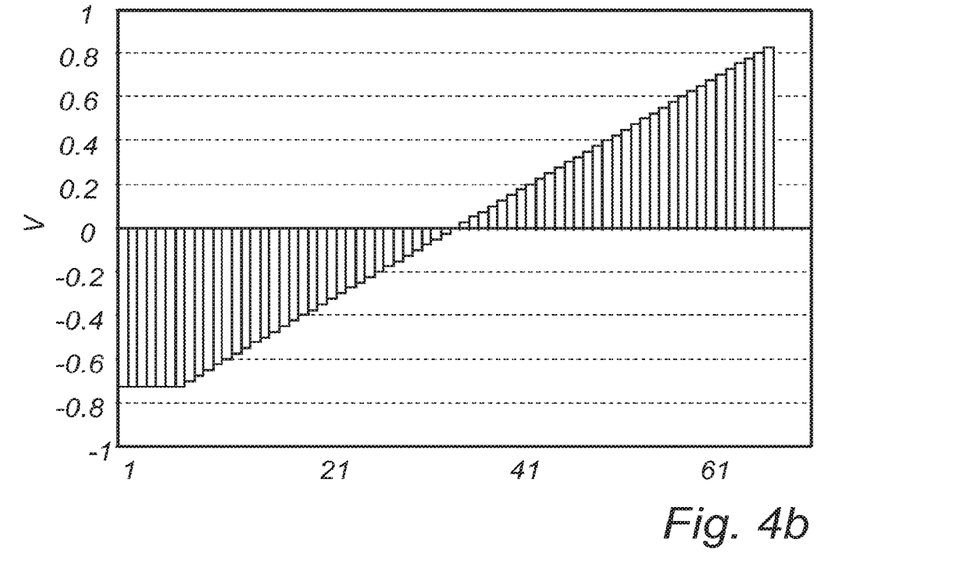
FIG. 4b is a simulation plot of voltage level pulses from a method according to an embodiment.
Figure 4C:
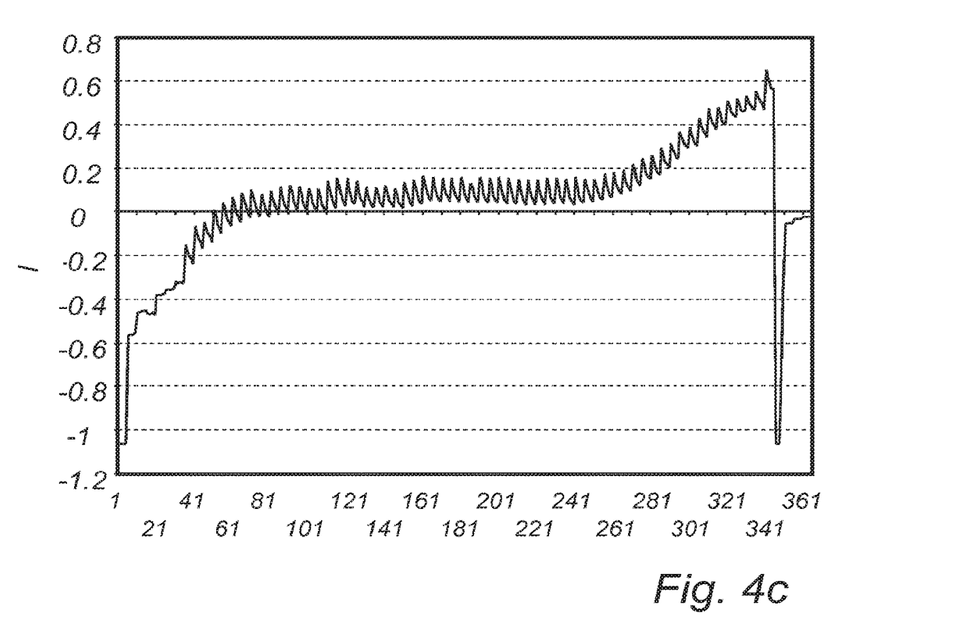
FIG. 4c is a simulation plot of a voltage corresponding to a current response generated by voltage pulses in FIG. 4b.

FIG. 4b further shows an example simulation of voltage pulses in a staircase pattern. The voltage level varies over time from approximately −0.75 V to approximately 0.8 V. The values on the x axis represent number of voltage pulses. FIG. 4c shows corresponding current responses as an outgoing voltage from an electronic circuit. Information from the current responses is used for estimating the sulphite level in the substance, using multivariate data analysis. Each voltage pulse as shown in FIG. 4b corresponds to five measured voltage values in FIG. 4c. Hence, in the example shown in FIGS. 4b and 4c, the response of each voltage pulse is measured five times during each voltage pulse. The values on the x axis of FIG. 4c represent number of measurements.

Figure 5A:
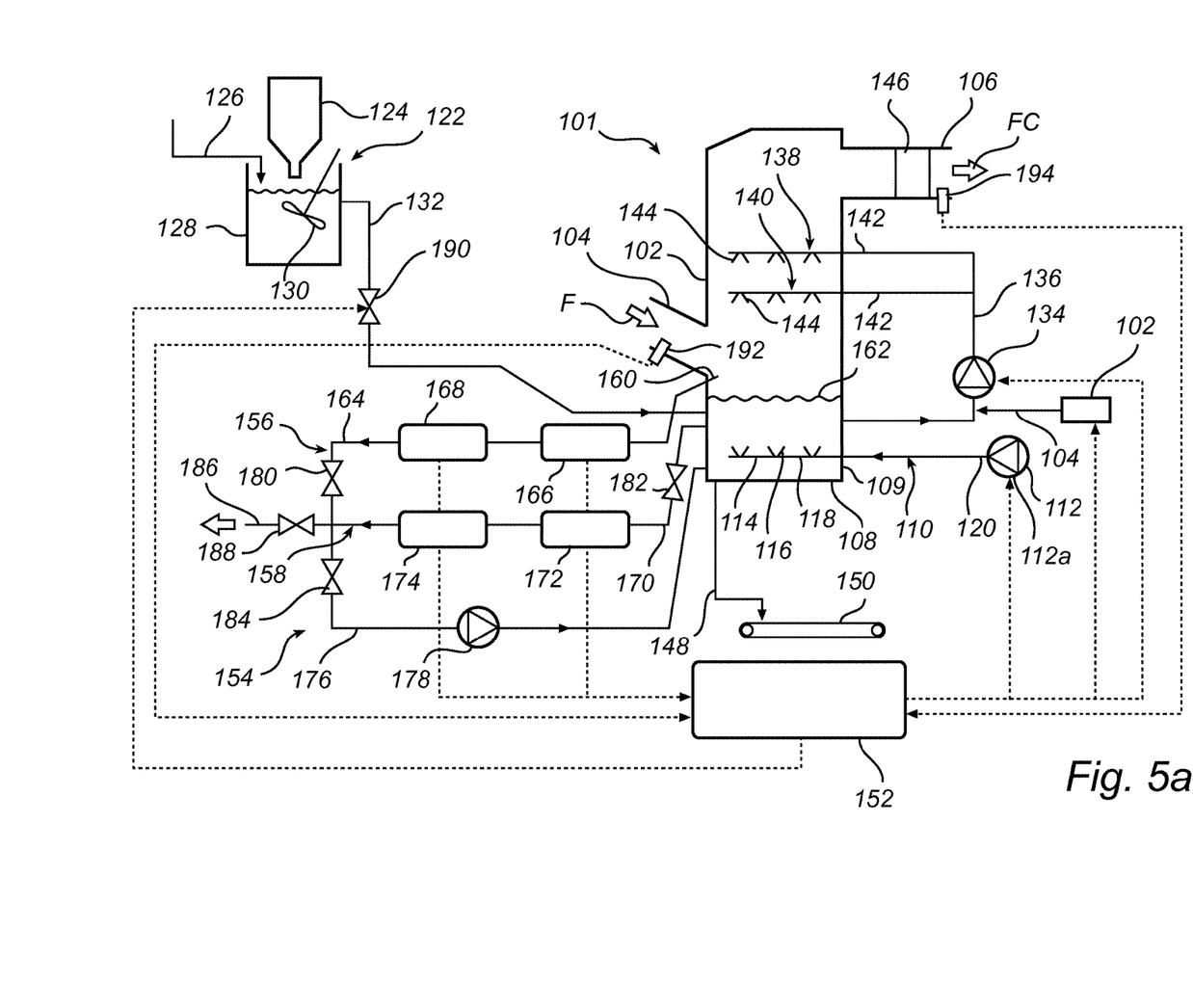
FIG. 5a is a schematic side cross sectional view of a wet scrubber comprising a sulphite sensor.

As an example application for a sulphite sensor 1 according to the invention, FIG. 5a illustrates a wet scrubber 101. The wet scrubber 101 is operative for removing at least a portion of the sulphur dioxide content of a process gas, in the form of a flue gas, F, generated in a boiler (not shown) which is operative for combusting a fuel, such as coal, oil, peat, natural gas, or waste material.

The wet scrubber 101 comprises an absorption vessel in the form of a vertical open tower 102, an inlet 104 for flue gas, F, to be cleaned, and an outlet 106 for flue gas, FC, from which at least a portion of the sulphur dioxide content has been removed.

An absorption liquid oxidation vessel in the form of an absorption liquid tank 108 is arranged at the bottom 109 of the vertical open tower 102. The absorption liquid tank 108 fulfils the dual purposes of being a recirculation tank for absorption liquid, and of being a vessel in which oxidation may occur. For the latter reason, the absorption liquid tank 108 is provided with an oxidation arrangement 110. The oxidation arrangement 110 comprises an oxygen gas supply device 112 in the form a blower 112a, an oxygen distributor 114 comprising a number of nozzles 116 arranged on a distributing pipe 118, and a supply pipe 120 being fluidly connected to the blower 112 and to the distributing pipe 118 for supplying compressed oxygen containing gas, such as air, to the distributing pipe 118 and further to the nozzles 116. The nozzles 116 are arranged for distributing the air in a limestone absorption liquid contained in the absorption liquid tank 108 and to cause oxidation of sulphite contained in the limestone absorption liquid, as will be described in more detail hereinafter. It will be appreciated that the oxygen supply device 112 could, as alternative to a blower 112a, be a compressor or some other device suitable for forcing a gas containing oxygen into the absorption liquid of the absorption liquid tank 108. Furthermore, the oxygen containing gas blown by the blower 112a may, for example, be air, a rather pure oxygen gas, such as a gas comprising 90-99% by volume of oxygen, or a mixture of oxygen gas and air.

Absorbent material in the form of, for example, fresh limestone, $CaCO_3$, is supplied to the absorption liquid tank 108 from an absorbent supply system 122. The absorbent supply system 122 comprises a limestone silo 124, a water supply pipe 126, and a mixing tank 128 comprising an agitator 130. In the mixing tank 128 water supplied via fluidly connected supply pipe 126 is mixed with limestone powder supplied from limestone silo 124 to form limestone slurry. The limestone slurry is supplied from the mixing tank 128 to the absorption liquid tank 108 via a fluidly connected limestone supply pipe 132. It will be appreciated that absorption liquid tank 108 may, as an alternative, be positioned outside of tower 102, and that the supply of limestone could, as an alternative, enter the system at other locations, as a dry powder, a slurry or both. The limestone, $CaCO_3$, may be at least partly dissolved in the water:

$$CaCO_3\ (s) + H_2O \Longleftrightarrow Ca^{2+}\ (aq) + CO_3^{2-}\ (aq) \qquad [eq.\ 1]$$

The wet scrubber 101 further comprises a scrubber circulation pump 134 which circulates, in absorption liquid circulation pipe 136, the limestone absorption liquid, from the absorption liquid tank 108 to two spray level systems 138, 140 positioned within open tower 102.

Each spray level system 138, 140 comprises a piping system 142 and a number of fluidly connected atomizing nozzles 144 that finely distribute limestone absorption liquid, circulated by the pump 134, to achieve effective contact between the limestone absorption liquid and the flue gas F passing through the wet scrubber 101 and flowing substantially vertically upwards inside open tower 102. All or some of the atomizing nozzles 144 may, for example, be of the type 4CF-303120, available from Spraying Systems Co, Wheaton, Ill., USA. In the open tower 102 of the wet scrubber 101 the following reaction will occur upon absorption of sulphur dioxide, $SO_2$, comprised in the flue gas F by the limestone absorption liquid finely distributed by the nozzles 144:

$$SO_2\ (g) + CO_3^{2-}\ (aq) + Ca^{2+}\ (aq) \Longleftrightarrow CaSO_3\ (aq) + CO_2\ (g) \qquad [eq.\ 2]$$

A mist eliminator 146 is located downstream of the spray level systems 138, 140. The mist eliminator 146 removes at least a portion of the absorption liquid droplets entrained by the cleaned flue gas, FC.

In the wet scrubber 101, sulphur dioxide, $SO_2$, in the flue gas F reacts with the limestone, $CaCO_3$, to form calcium sulphite, $CaSO_3$, which is subsequently oxidized to form gypsum, $CaSO_4$. The oxidation of calcium sulphite is performed by bubbling an oxygen containing gas, such as air, through the limestone absorption liquid using oxidation arrangement 110. The following reaction may occur in the absorption liquid tank 108:

$$CaSO_3\ (aq) + \tfrac{1}{2}O_2\ (g) \Longleftrightarrow CaSO_4\ (s) + 2H_2O \qquad [eq.\ 3]$$

Hence, gypsum, $CaSO_4$, sometimes described as including two water molecules, i.e., $CaSO_4 \times 2H_2O$, is formed as the end product. Hereinbefore, it has been described that the absorption of $SO_2$ generates calcium sulphite $CaSO_3$. It will be appreciated that, depending on the conditions, at least a portion of the absorbed $SO_2$ would generate calcium bisulphite, $Ca(HSO_3)_2$ (aq), which would be oxidized according to principles similar to that of [eq. 3] above.

Hence, the limestone absorption liquid comprises, in addition to the limestone, also small amounts of calcium sulphite and, as major constituent, gypsum. The gypsum formed through this process is removed from the wet scrubber 101 via a disposal pipe 148 and is forwarded to a gypsum dewatering unit, schematically indicated as belt filter 150. The dewatered gypsum may be commercially used, for example in wallboard production.

In addition to sulphur dioxide, $SO_2$, the wet scrubber 101 will remove, at least partly, also other contaminants from the flue gas. Examples of such other contaminants include sulphur trioxide, $SO_3$, hydrochloric acid, HCl, hydrofluoric acid, HF, and other acid contaminants. Still further, the wet scrubber 101 may also remove, at least partly, also other types of contaminants from the flue gas, such as for example dust particles and mercury.

A control unit 152 controls the operating parameters of wet scrubber 101. The wet scrubber 101 is provided with an absorption liquid sampling system 154, which supplies measured data to the control unit 152. The sampling system 154 comprises a direct sampling train 156 and an absorption liquid tank sampling train 158.

The direct sampling train 156 comprises a scoop 160 for catching droplets of absorption liquid just above a surface 162 of the absorption liquid in the tank 108. The droplets of absorption liquid caught by the scoop 160 are droplets that have been atomized by nozzles 144, and have passed through the open tower 102 under absorption of sulphur dioxide, $SO_2$, but that have not yet been exposed to the oxidation of the oxidation arrangement 110. The droplets of absorption liquid caught by the scoop 160 have not yet been brought into contact with the absorbent material supplied via absorbent supply system 122. The absorption liquid caught by the scoop 160 is forwarded, via a fluidly connected pipe 164 to a first pH analyser 166, and a first sulphite analyser 168. The first sulphite analyser 168 comprises a sulphite sensor 1.

The absorption liquid tank sampling train 158 comprises a pipe 170 fluidly connected to the absorption liquid tank 108. The absorption liquid collected from tank 108 by pipe 170 is forwarded, via pipe 170, to a second pH analyser 172, and a second sulphite analyser 174. The oxidation arrangement 110 arrangement causes an agitation of the absorption liquid contained in the tank 108, and, hence, the tank 108 may be regarded as a continuously stirred tank reactor in which the oxidation reaction occurs. Optionally, a further agitator may be arranged in the tank 108.

The pipes 164 and 170 are fluidly connected to a circulation pipe 176. A circulation pump 178 is arranged in circulation pipe 176 for pumping absorption liquid, having passed through direct sampling train 156 and absorption liquid tank sampling train 158, back to absorption liquid tank 108. Shut-off valves 180, 182, 184 arranged in the pipes 164, 170 and 176, respectively, makes it possible to collect an absorption liquid sample, via sampling pipe 186 and associated shut off valve 188, for manual analysis of the sulphite concentration and/or the pH of absorption liquid collected via direct sampling train 156 or absorption liquid tank sampling train 158.

Control unit 152 receives measurement signals from analysers 166, 168, 172 and 174, and controls, based on such measurement signals, at least one of: a control valve 190 arranged in limestone supply pipe 132 and controlling the amount of limestone slurry supplied from the mixing tank 128 to the absorption liquid tank 108, the scrubber circulation pump 134, and the blower 112 of the oxidation arrangement 110. Furthermore, the control unit 152 may also receive measurement signals from a first $SO_2$ analyser 192 measuring the concentration of $SO_2$ in the flue gas F entering the open tower 102 of the wet scrubber 101, and a second $SO_2$ analyser 194 measuring the concentration of $SO_2$ in the cleaned flue gas FC leaving the open tower 102 of the wet scrubber 101.

Figure 5B:
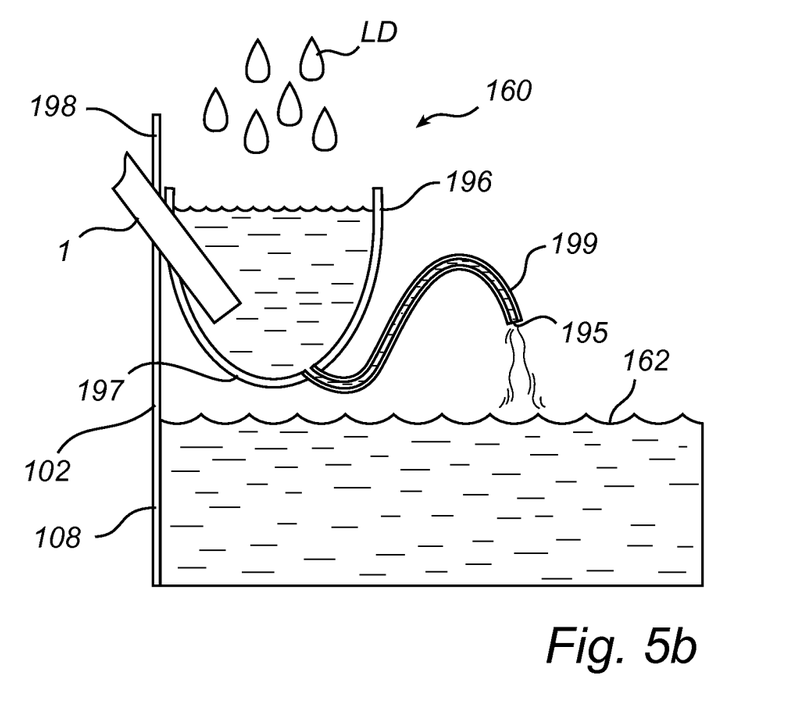
FIG. 5b is an enlarged schematic side cross sectional view of a scoop according to an alternative embodiment.

FIG. 5b illustrates a scoop 160 according to an alternative embodiment. The scoop 160 is arranged entirely within the open tower 102 and comprises a funnel portion 196 arranged inside the open tower 102, above the surface 162 of absorption liquid contained in the absorption liquid tank 108. Liquid droplets LD generated by nozzles 144 illustrated in FIG. 5a and falling downwardly inside open tower 102 are collected in the funnel portion 196. The funnel portion 196 is connected, at a bottom 197 thereof, to an "S"-shaped drain pipe 199. The drain pipe 199 will function as a water trap ensuring that an amount of collected liquid is present in funnel portion 196. A mouth 195 of the drain pipe 199 opens above the surface 162 to avoid any siphoning effects. A first sulphite analyser 168 extends into the open tower 102 and into the collected absorption liquid in the funnel portion 196. The first sulphite analyser 168 may comprise the sulphite sensor 1 described hereinbefore with reference to FIGS. 1-4. The funnel portion 196 and the drain pipe 199 ensure that the sulphite sensor 1 measures the sulphite concentration in freshly collected absorption liquid.

Figure 6A:
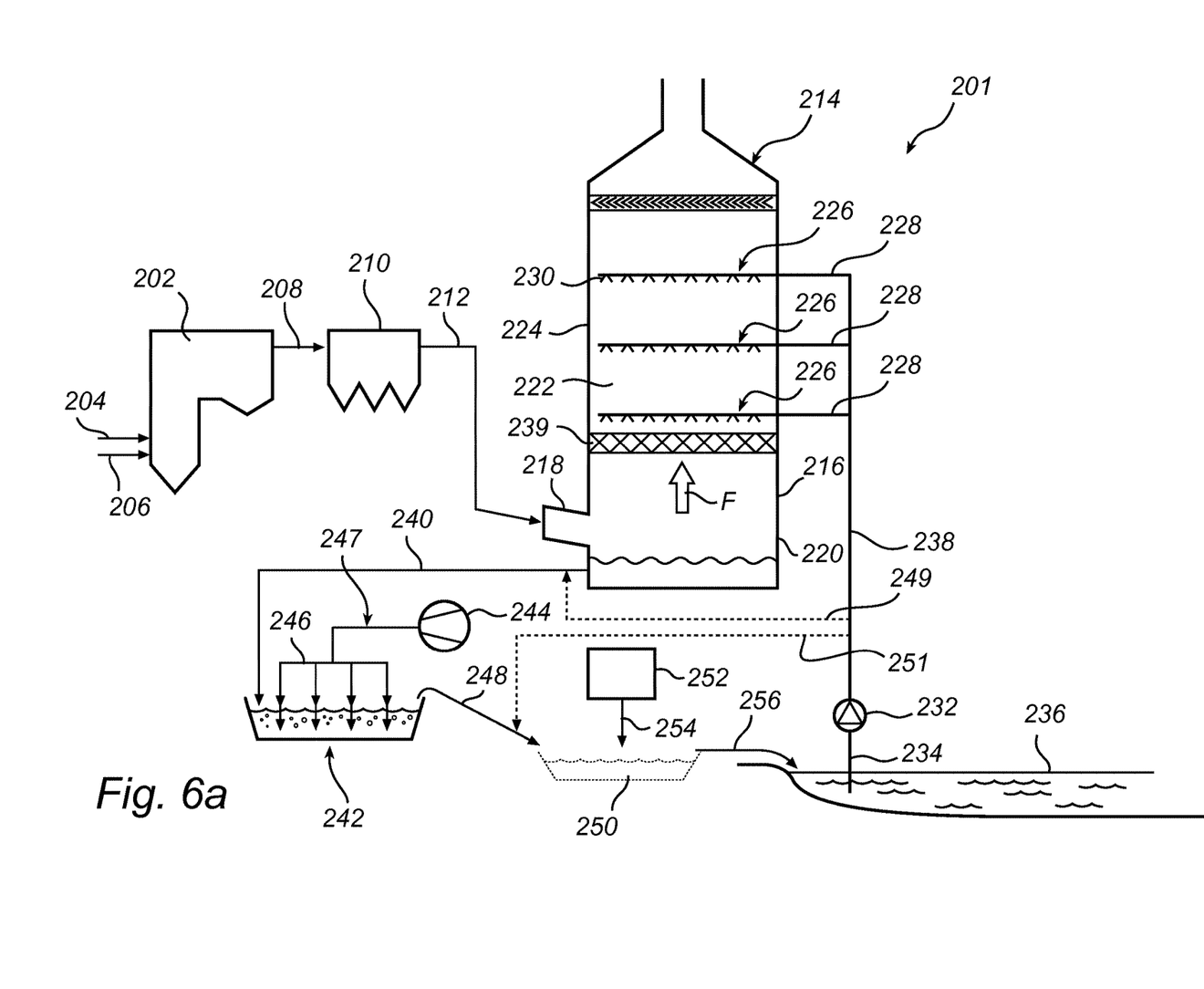
FIG. 6a is a schematic side cross sectional view of a power plant with a seawater based gas cleaning system.

A further example application for a sulphite sensor 1 is illustrated in FIG. 6*a* showing a schematic side cross-sectional view illustrating a power plant 201. The power plant 201 comprises a boiler 202 in which a fuel, such as coal, oil, peat, natural gas, or waste, supplied via feeding pipe 204 is combusted in the presence of oxygen, supplied via oxygen supply duct 206. The oxygen may, for example, be supplied in the form of air, and/or in the form of a mixture of oxygen gas and recirculated gases, in case the boiler 202 would be a so-called oxy-fuel boiler. The combustion of the fuel generates a hot process gas in the form of a flue gas. Sulfur species contained in the fuel upon combustion form sulfur dioxide, $SO_2$, which will form part of the flue gas.

The flue gas may flow from the boiler 202, via a fluidly connected duct 208, to an optional dust removal device in the form of an electrostatic precipitator 210. The electrostatic precipitator 210, an example of which is described in U.S. Pat. No. 4,502,872, serves to remove dust particles from the flue gas. As alternative, another type of dust removal device may be used, for example a fabric filter, an example of which is described in U.S. Pat. No. 4,336,035.

The flue gas, from which most of the dust particles have been removed, flows from the electrostatic precipitator 210, via a fluidly connected duct 212, to a seawater scrubber 214. The seawater scrubber 214 comprises a wet scrubber tower 216. An inlet 218 is arranged at a lower portion 220 of the wet scrubber tower 216. The duct 212 is fluidly connected to the inlet 218, such that flue gas flowing from electrostatic precipitator 210 via duct 212 may enter interior 222 of wet scrubber tower 216 via inlet 218.

After entering interior 222, flue gas flows vertically upward through wet scrubber tower 216, as indicated by arrow F. Central portion 224 of wet scrubber tower 216 is equipped with a number of spray arrangements 226 arranged vertically one above each other. In the example of FIG. 5*a*, there are three such spray arrangements 226, and typically there are 1 to 20 such spray arrangements 226 in a wet scrubber tower 216. Each spray arrangement 226 comprises a supply pipe 228 and a number of nozzles 230 fluidly connected to the respective supply pipe 228. Seawater supplied via the respective supply pipes 228 to the nozzles 230 is atomized by means of the nozzles 230 and is brought into contact, in interior 222 of wet scrubber tower 216, with the flue gas to absorb sulfur dioxide, $SO_2$, from the flue gas.

A pump 232 is arranged for pumping seawater via fluidly connected suction pipe 234 from ocean 236, and forwarding the seawater via fluidly connected pressure pipe 238 to fluidly connected supply pipes 228.

In accordance with an alternative embodiment, the seawater supplied by pump 232 to pipes 228 may be seawater previously utilized as cooling water in steam turbine systems associated with the boiler 202 prior to such seawater being utilized as scrubbing water in the seawater scrubber 214.

Seawater atomized by means of nozzles 230 in interior 222 of wet scrubber tower 216 flows downward in wet scrubber tower 216 and absorbs sulfur dioxide from the flue gas F flowing vertically upward in interior 222 of wet scrubber tower 216. As a result of such absorption of sulfur dioxide the seawater gradually turns into effluent seawater while moving downward in interior 222 of wet scrubber tower 216. Effluent seawater is collected in lower portion 220 of the wet scrubber tower 216 and is forwarded, via fluidly connected effluent pipe 240, from the wet scrubber tower 216 to an oxidation basin system 242.

In accordance with an alternative embodiment, the seawater scrubber 214 may comprise one or more layers of a packing material 239 arranged in interior 222 of wet scrubber tower 216. The packing material 239, which may be made from plastic, steel, wood, or another suitable material, enhances gas-liquid contact. With packing material 239, the nozzles 230 would merely distribute seawater over packing material 239, rather than atomizing the seawater. Examples of packing material 239 include Mellapak™ available from Sulzer Chemtech AG, Winterthur, CH, and Pall™ rings available from Raschig GmbH, Ludwigshafen, DE.

Optionally, fresh seawater may be added to the effluent seawater prior to further treatment of the effluent seawater. To this end, a pipe 249 may be fluidly connected to pressure pipe 238 to forward a flow of fresh seawater to fluidly connected effluent pipe 240 forwarding effluent seawater to oxidation basin system 242. Hence, an intermixing of fresh seawater and effluent seawater occurs in pipe 240. As an alternative, the fresh seawater forwarded via pipe 249 may be forwarded directly to oxidation basin system 242 for being mixed with the effluent seawater therein. As a still further option, residual waters and/or condensates generated in the boiler 202 or steam turbine systems associated therewith could be mixed with the effluent seawater.

Figure 6B:
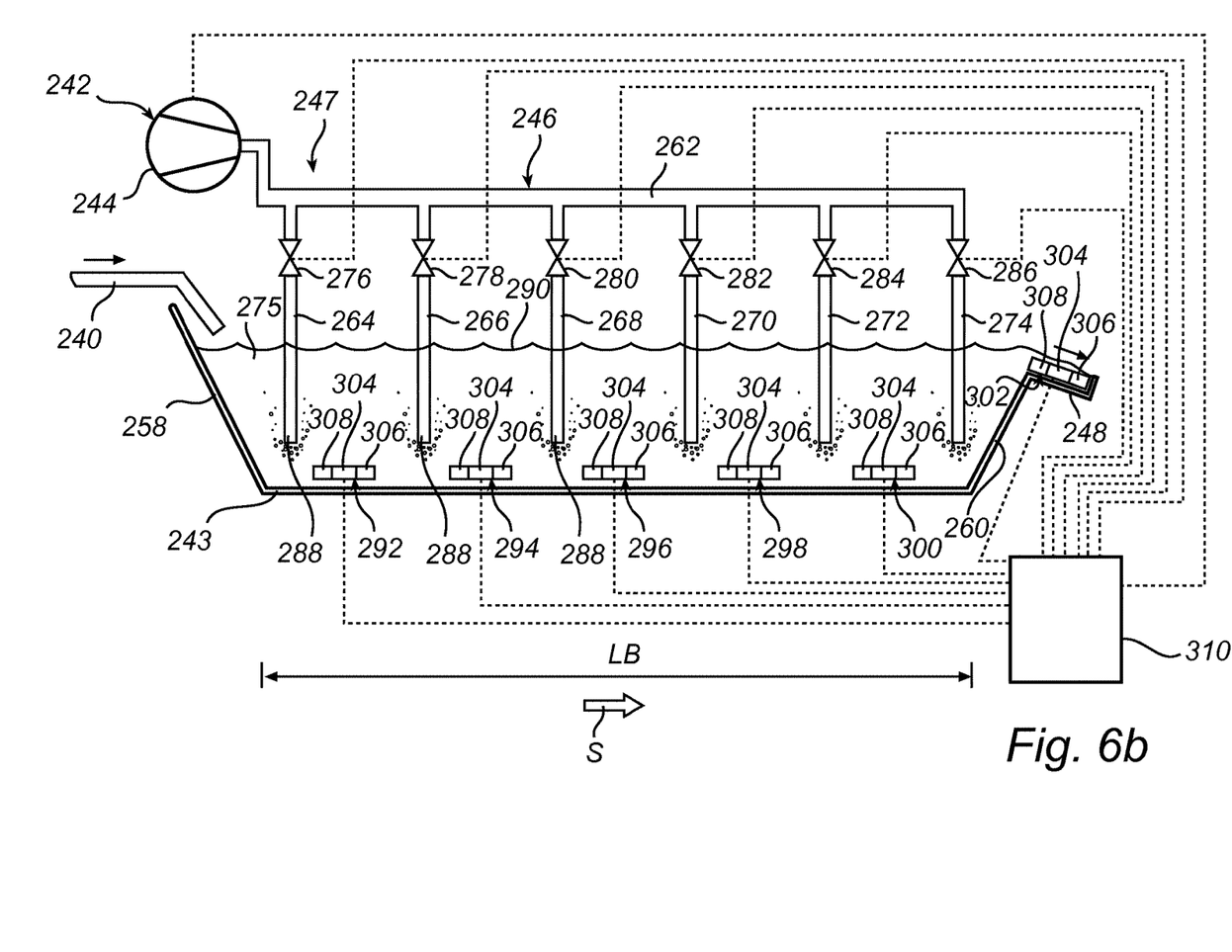
FIG. 6b is a schematic side cross sectional view illustrating an oxidation basin system in a gas cleaning system.

The oxidation basin system 242 comprises a blowing device in the form of a compressor or a blower 244 which is arranged for blowing, via fluidly connected ductwork 246, an oxygen containing gas, such as air, into the effluent seawater. The blower 244 and the ductwork 246 together form an oxygen supply system 247 for supplying oxygen to the effluent seawater. A more detailed description of the oxidation basin system 242 will be given hereinafter with reference to FIG. 5*b*.

Optionally, the effluent seawater may be forwarded, via a fluidly connected overflow pipe 248, from the oxidation basin system 242 to an alkalization basin 250. Storage 252 of alkali agent is, optionally, arranged for supplying alkali agent, via fluidly connected pipe 254, to basin 250. The alkali agent may, for example, be limestone or fresh seawater from the ocean, which serves to increase the pH of the effluent seawater if needed.

The effluent seawater is, finally, forwarded via a fluidly connected overflow pipe 256 from the alkalization basin 250 and back to the ocean 236.

In accordance with an alternative embodiment, the effluent seawater forwarded via overflow pipe 248 is forwarded directly to the ocean 236 without passing any alkalization basin. In accordance with a further alternative embodiment, the effluent seawater is mixed with fresh seawater prior to being discharged into the ocean 236. To this end a pipe 251 may be fluidly connected to pressure pipe 238 to forward a flow of fresh seawater to fluidly connected overflow pipe 248. Hence, an intermixing of fresh seawater and effluent seawater occurs in pipe 248.

FIG. 6*b* illustrates the oxidation basin system 242 in more detail. Effluent seawater is supplied to an oxidation basin 243 of the oxidation basin system 242 via fluidly connected duct 240 at a first end 258, being an inlet end, of oxidation basin 243. The effluent seawater flows, generally horizontally as indicated by arrow S, along the length LB of the oxidation basin 243, from the first end 258 to a second end 260, being an outlet end, of oxidation basin 243. At the second end 260, the effluent seawater overflows into fluidly connected overflow pipe 248 and leaves basin 243.

Oxidation basin system 242 further includes the oxygen supply system 247 having the ductwork 246. The ductwork 246 comprises a central distribution duct 262 extending horizontally along the basin 243 from a position adjacent to the first end 258 to a position adjacent to the second end 260. The ductwork 246 further comprises first, second, third, fourth, fifth, and sixth consecutive air distribution pipes 264, 266, 268, 270, 272, 274 which are fluidly connected to the central distribution duct 262 and extend into the effluent seawater 275 flowing horizontally through the basin 243. The six air distribution pipes 264, 266, 268, 270, 272, 274 are arranged consecutively along the length LB of the basin 243, with the first air distribution pipe 264 being located closest to the first end 258, the second air distribution pipe 266 located downstream of the first pipe 264, etc., with the sixth air distribution pipe 274 being located closest to the second end 260. Each of the air distribution pipes 264, 266, 268, 270, 272, 274 is provided with a respective control device in the form of a control valve 276, 278, 280, 282, 284, 286 which may be controlled to control the flow of oxygen containing gas, such as air, through the respective air distribution pipe 264, 266, 268, 270, 272, 274. Blower 244 blows air into central distribution duct 262 and further into air distribution pipes 264, 266, 268, 270, 272, 274. The lower ends 288 of air distribution pipes 264, 266, 268, 270, 272, 274 are open and are arranged below liquid surface 290 of effluent seawater 275 in oxidation basin 243. Air blown by blower 244 is forwarded, via central distribution duct 262 and air distribution pipes to open lower ends 288. At open ends 288 the air is dispersed and mixed with the effluent seawater. At least a portion of the oxygen content of the air thus dispersed and mixed with effluent seawater is dissolved in the effluent seawater and reacts to oxidize sulphite and/or bisulfate ions in accordance with reactions described hereinafter.

In accordance with an alternative embodiment, the oxygen supply system 247 may be operative for blowing an oxygen rich gas, comprising more than 21% by volume of oxygen, for example comprising 75-100% by volume of oxygen, into the effluent seawater of the oxidation basin 243.

Oxidation basin system 242 may further comprise first, second, third, fourth, and fifth consecutive water quality sensors 292, 294, 296, 298, 300, which are immersed in the effluent seawater 275 flowing through the basin 243. The five water quality sensors 292, 294, 296, 298, 300 are arranged consecutively along the length LB of the basin 243, with the first water quality sensor 292 being located closest to the first end 258, the second water quality sensor 294 located downstream of the first sensor 292, etc., with the fifth sensor being located closest to the second end 260. A sixth, and last, water quality sensor 302 is arranged in the overflow pipe 248. Each water quality sensor 292, 294, 296, 298, 300, 302 may comprise one or more detecting elements. In the embodiment illustrated in FIG. 5b, each water quality sensor comprises a sulphite detecting element 304, an oxygen detecting element 306, and a pH detecting element 308. The sulphite detecting element 304 comprises a sulphite sensor 1.

Each water quality sensor 292, 294, 296, 298, 300, 302 is arranged for detecting one or more parameters of the effluent seawater, as measured in that specific position at which the water quality sensor in question is arranged, and for sending a signal to a control unit 310. The control unit 310, which may be a process control computer, analyses the signals received from the respective water quality sensors 292, 294, 296, 298, 300, 302, and automatically controls the setting of the respective control valve 276, 278, 280, 282, 284, 286 such that a suitable flow of oxygen containing gas is supplied to the effluent seawater via each of the air distribution pipes 264, 266, 268, 270, 272, 274. The control unit 310 may also automatically control the output of the blower 244, such that a suitable amount of air is supplied to the ductwork 246 and further to the air distribution pipes 264, 266, 268, 270, 272, 274.

While the present invention has been described with reference to a number of preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for measuring a concentration of sulphite in an absorption liquid of a wet scrubber used in a gas cleaning process, the method comprising steps of:
   sending a plurality of voltage pulses through the absorption liquid of the wet scrubber using a first electrode and a second electrode that are in contact with the absorption liquid of the wet scrubber, wherein sending a plurality of voltage pulses comprises sending the plurality of voltage pulses in a stepwise series having a stepwise increase or a stepwise decrease of voltage level between consecutive pulses;
   receiving current responses generated by the plurality of voltage pulses sent in the stepwise series;
   analyzing the current responses by analyzing at least two separate values of each current response generated by the plurality of voltage pulses sent in the stepwise series; and
   calculating the concentration of sulphite in the absorption liquid of the wet scrubber based on the at least two separate values of each current response generated by the plurality of voltage pulses sent in the stepwise series.

2. The method according to claim 1, wherein each voltage pulse sent through the absorption liquid of the wet scrubber is 0.02-0.2 V higher or lower than an immediately preceding voltage pulse.

3. The method according to claim 1, wherein the step of analyzing the at least two separate values comprises analyzing a peak value and at least one more value of each of the current responses.

4. The method according to claim 1, wherein the method further comprises cleaning a surface of the first electrode by removing a coating from the first electrode caused by contact between the first electrode and the absorption liquid of the wet scrubber.

5. The method according to claim 1, wherein the method further comprises cleaning a surface of the first electrode by rotating a cleaning unit in contact with the first electrode.

6. The method according to claim 1, further comprising cleaning the first electrode using a cleaning unit rotated in contact with a surface of the first electrode at a speed of 2-40 rpm.

7. The method according to claim 1, further comprising providing a sensor for measuring another property of the absorption liquid of the wet scrubber.

8. The method according to claim 1, further comprising providing a sensor for measuring a temperature of the absorption liquid of the wet scrubber.

* * * * *